(12) United States Patent
Leyva et al.

(10) Patent No.: US 10,524,613 B2
(45) Date of Patent: Jan. 7, 2020

(54) TECHNOLOGIES FOR SANITIZING BEVERAGE MAKERS

(71) Applicant: SoClean, Inc., Peterborough, MA (US)

(72) Inventors: Timothy Leyva, Bellingham, MA (US); Tahira Jayasuriya, Peterborough, NH (US)

(73) Assignee: SoClean, Inc., Peterborough, NH (US)

( * ) Notice: Subject to any disclaimer, the term of this patent is extended or adjusted under 35 U.S.C. 154(b) by 0 days.

(21) Appl. No.: 15/499,167

(22) Filed: Apr. 27, 2017

(65) Prior Publication Data

US 2018/0310756 A1  Nov. 1, 2018

(51) Int. Cl.
| | | |
|---|---|---|
| *A61L 9/00* | (2006.01) | |
| *A61L 2/00* | (2006.01) | |
| *A61L 2/08* | (2006.01) | |
| *A47J 31/60* | (2006.01) | |
| *A61L 2/20* | (2006.01) | |

(52) U.S. Cl.
CPC .............. *A47J 31/60* (2013.01); *A61L 2/202* (2013.01); *A61L 2202/11* (2013.01); *A61L 2202/13* (2013.01); *A61L 2202/14* (2013.01)

(58) Field of Classification Search
CPC ........... A61L 2/183; F25C 5/185; C01B 13/11
USPC ................. 422/1, 26, 28, 292, 305
See application file for complete search history.

(56) References Cited

U.S. PATENT DOCUMENTS

| | | | |
|---|---|---|---|
| 4,257,748 A | 3/1981 | Ives et al. | |
| 4,482,172 A | 11/1984 | DeVera et al. | |
| 4,762,343 A | 8/1988 | Hirohata | |
| 4,922,971 A | 5/1990 | Grantham | |
| 5,683,576 A | 11/1997 | Olsen | |
| 6,074,565 A | 6/2000 | Buckner | |
| 6,609,733 B2 | 8/2003 | Gilmore | |
| 7,240,700 B2 | 7/2007 | Pangallo et al. | |
| 7,472,929 B2 | 1/2009 | Fattorusso et al. | |
| 7,491,321 B1 | 2/2009 | Maas et al. | |
| 7,767,168 B2 | 8/2010 | Namespetra et al. | |
| 8,298,492 B2 * | 10/2012 | Shiotani ............... | B67D 3/0009 210/192 |
| 9,956,309 B1 | 5/2018 | Leyva | |
| 9,962,627 B1 | 5/2018 | Leyva | |

(Continued)

FOREIGN PATENT DOCUMENTS

| | | |
|---|---|---|
| DE | 9104578.9 | 8/1992 |
| FR | 1529814 | 5/1968 |

(Continued)

OTHER PUBLICATIONS

Notice of Allowance dated Dec. 14, 2017, issued in U.S. Appl. No. 15/499,070, 5 pages.

(Continued)

*Primary Examiner* — Monzer R Chorbaji
(74) *Attorney, Agent, or Firm* — Grossman Tucker Perreault & Pfleger PLLC (57) ABSTRACT

Technologies (e.g., devices, systems and methods) for sanitizing hot beverage makers are described. In some embodiments, the technologies include a sanitization gas system that is configured to be install into a cover, onto a wall or cover and between a the top rim of the reservoir and the cover of the reservoir. The sanitization gas system may provide a sanitizing gas to the reservoir for sanitizing the reservoir, sidewalls, bottom tray and cover.

20 Claims, 4 Drawing Sheets

(56) References Cited

U.S. PATENT DOCUMENTS

| | | | |
|---|---|---|---|
| 9,986,871 | B1 | 6/2018 | Leyva |
| 10,264,913 | B2 | 4/2019 | Leyva |
| 10,322,199 | B2 | 6/2019 | Leyva |
| 2003/0049164 | A1 | 3/2003 | Bon et al. |
| 2004/0051308 | A1 | 3/2004 | Coates |
| 2009/0039033 | A1 | 2/2009 | Kee et al. |
| 2010/0170857 | A1 | 7/2010 | Williams et al. |
| 2014/0154134 | A1 | 6/2014 | Leyva |
| 2015/0050194 | A1 | 2/2015 | Li |
| 2016/0102785 | A1 | 4/2016 | Bibbo et al. |
| 2016/0242596 | A1 | 8/2016 | Bennett |
| 2018/0310756 | A1 | 11/2018 | Leyva |
| 2018/0310757 | A1 | 11/2018 | Leyva |
| 2018/0311391 | A1 | 11/2018 | Leyva |
| 2018/0311595 | A1 | 11/2018 | Leyva |
| 2019/0261810 | A1 | 8/2019 | Leyva |
| 2019/0262491 | A1 | 8/2019 | Leyva |

FOREIGN PATENT DOCUMENTS

| | | |
|---|---|---|
| GB | 658755 | 10/1951 |
| WO | 2018200500 | 11/2018 |
| WO | 2018200504 | 11/2018 |
| WO | 2018200514 | 11/2018 |
| WO | 2018200519 | 11/2018 |

OTHER PUBLICATIONS

Notice of Allowance dated Dec. 18, 2017, issued in U.S. Appl. No. 15/498,954 5 pages.
Notice of Allowance dated Feb. 7, 2018, issued in U.S. Appl. No. 15/498,884, 5 pages.
Office Action dated Aug. 23, 2017, issued in U.S. Appl. No. 15/498,884, 8 pages.
Office Action dated Aug. 23, 2017, issued in U.S. Appl. No. 15/499,070, 8 pages.
Office Action dated Aug. 30, 2017, issued in U.S. Appl. No. 15/498,954, 7 pages.
Office Action dated May 7, 2018, issued in U.S. Appl. No. 15/928,287, 8 pages.
Office Action dated May 15, 2018, issued in U.S. Appl. No. 15/919,833, 8 pages.
International Search Report and Written Opinion dated May 21, 2018, issued in PCT Patent Application No. PCT/US2018/029127, 7 pages.
International Search Report and Written Opinion dated Jun. 4, 2018, issued in PCT Patent Application No. PCT/US2018/029133, 9 pages.
International Search Report and Written Opinion dated Jul. 13, 2018, issued in PCT Patent Application No. PCT/US2018/029115, 12 pages.
International Search Report and Written Opinion dated Jul. 19, 2018, issued in PCT Patent Application No. PCT/US2018/029111, 13 pages.
Office Action dated Jul. 13 2018, issued in U.S. Appl. No. 15/969,427, 7 pages.
Notice of Allowance dated Feb. 4, 2019, issued in U.S. Appl. No. 15/919,833, 6 pages.
Notice of Allowance dated May 24, 2019, issued in U.S. Appl. No. 15/928,287, 5 pages.
Notice of Allowance dated Dec. 12, 2018, issued in U.S. Appl. No. 15/969,427, 5 pages.
Office Action dated Oct. 29, 2018, issued in U.S. Appl. No. 15/919,833, 9 pages.
Office Action dated Dec. 4, 2018, issued in U.S. Appl. No. 15/928,287, 6 pages.
Notice of Allowance dated Jul. 25, 2019, issued in U.S. Appl. No. 15/928,287, 5 pages.

* cited by examiner

TECHNOLOGIES FOR SANITIZING BEVERAGE MAKERS

FIELD

The present disclosure generally relates to technologies for sanitizing beverage makers, including but not limited to hot beverage makers (e.g., coffee and tea making machines). In particular, the present disclosure relates to devices and systems for sanitizing a water reservoir of a beverage maker (and optionally any water therein) with a sanitizing gas such as ozone. Methods of sanitizing a beverage maker are also disclosed.

BACKGROUND

Hot beverage makers (e.g., coffee and tea making machines such as the commonly used KEURIG® coffee maker) often have one or more reservoirs for holding water. In response to an input from a user, water in the reservoir may be drawn into a hot beverage maker and used to make a hot beverage of the user's choice.

Although many hot beverage makers are infrequently cleaned, users of such machines often assume that they are safe to drink from because the water they use is heated prior to being dispensed. This understanding may be incorrect, however, as many hot beverage makers do not heat water to a sufficiently high temperature (e.g. boiling) to adequately kill bacteria in the water prior to it being dispensed for consumption. Live bacteria and/or other contaminants may therefore remain in water that is dispensed by a hot beverage maker for consumption. Water in the reservoir of a hot beverage maker may also remain stagnant for long periods (e.g. days) before it is replaced or replenished with fresh water—providing an opportunity for mold and bacteria to build up on the walls and bottom of the reservoir, as well as in the water itself. Despite this risk, users of hot beverage makers often do not clean the reservoir or replenish the reservoir with fresh water when the water therein has been sitting for a long period of time.

The foregoing issues are compounded by the fact that many commonly recommended methods for cleaning hot beverage makers can be messy, time consuming, and inconvenient. For example, the user guide of some hot beverage makers may recommend cleaning the reservoir and/or other components of the machine using a cleaning solution that is a mixture of water and vinegar. Such methods can be inconvenient, as they often require the user to prepare the cleaning solution themselves. Moreover, such a cleaning solution may not effectively kill some types of water born mold and/or bacteria, and therefore may inadequately sanitize the reservoir of a hot beverage maker. Other commonly recommended methods of cleaning a hot beverage maker include manual washing, scrubbing, and drying of the reservoir, which are often time consuming and considered to be undesirable to consumers.

Accordingly the inventors have identified that there is a continued interest in the development of novel devices, systems, and methods for sanitizing all or a portion of a beverage maker, including but not limited to the water reservoir of a beverage maker and any water therein.

BRIEF DESCRIPTION OF THE DRAWINGS

Reference is now made to the following detailed description which should be read in conjunction with the following figures, wherein like numerals represent like parts.

DETAILED DESCRIPTION

As explained in the background consumers often believe that beverage makers (and in particular hot beverage makers) are safe to drink from, even though such machines may be rarely cleaned and may provide conditions that facilitate the growth of mold and/or bacteria. Although there are various known methods for cleaning beverage makers, such methods are often inconvenient, messy, time-consuming, etc., and therefore may be rarely performed by consumers. Such methods may also inadequately sanitize a beverage maker, and in particular the reservoir thereof and any water therein. The inventors have therefore identified that there is a need in the art for technologies (e.g., devices, systems and methods) that enable convenient, easy and effective sanitization of a beverage maker and, in particular, the reservoir of a beverage maker and any water therein.

With the foregoing in mind, aspects of the present disclosure relate to devices, systems and methods that utilize a sanitizing gas (e.g. ozone) to sanitize all or a portion of a beverage maker, such as but not limited to a reservoir thereof. As will be described in detail later, the devices, systems and methods of the present disclosure are particularly useful for sanitizing the reservoir of a hot beverage maker, including the bottom tray and sidewalls thereof. The technologies described herein are not limited to such applications, however, and can be utilized to sanitize a type of reservoir, such as those that may be used in soda fountains, animal watering machines, and the like.

Although the technologies described herein can be used with many sanitizing gases, the present disclosure focuses on the use of ozone as a sanitizing gas. This is because ozone ($O_3$) gas is an effective sanitizer, yet is relatively safe for consumer use. Indeed because of its strongly oxidizing properties, ozone can effectively kill or otherwise remove a wide range of organic and inorganic contaminants such as yeasts, bacteria, molds, viruses, other pathogens, and/or pollutants with which it comes into contact, e.g., via oxidation. Yet naturally over time and/or as it oxidizes contaminants, ozone may be chemically reduced to oxygen ($O_2$), which is safe for human consumption and for release into the environment. Ozone is also relatively easy to generate on site (and thus does not require the use of a storage tank), and leaves little or no chemical residue. For those and other reasons, ozone has been identified as a safe and effective sanitizing gas for use in the present disclosure. It should be understood, however, that the technologies described herein are not limited to the use of ozone, and may be employed with a wide variety of sanitizing gases.

Aspects of the present disclosure relate to technologies (e.g., devices, systems, and methods) for sanitizing all or a portion of a reservoir, such as but not limited to a liquid reservoir. For the sake of illustration the present disclosure focuses on embodiments in which the technologies described herein are employed to sanitize a water reservoir, bottom tray, side walls and any mist chamber of a hot beverage maker. It should be understood that such examples are for the sake of illustration only, and that the technologies described herein may be used to sanitize a wide variety of reservoirs that may be used in applications other than a hot beverage machine.

As used herein, the term "hot beverage maker" refers to any of a wide variety of machines that may be utilized to produce beverages for human or animal consumption, wherein the beverages are produced using water that is at a temperature that is greater than about 25 degrees Celsius, and which include a reservoir for holding water to be used by the machine. Non-limiting examples of hot-beverage makers include coffee making machines (e.g., the well-known KEURIG® coffee makers), espresso making machines, tea making machines, combinations thereof, and the like.

As used herein, the term "fluidly coupled" means that two or more components are connected to one another such that a gas may be conveyed between them. In contrast, the term "coupled" when used alone means that two or more components are connected to one another chemically (e.g., via an adhesive), mechanically (e.g., via fasteners, mechanical interference, etc.), or by other means.

One aspect of the present disclosure relates to systems for sanitizing a reservoir, e.g., of a hot beverage maker. As will be described further below, the systems described herein generally include a gas supply system, a supply line, and an exhaust system. The gas supply system, the supply line and all or a portion of the exhaust system are configured to be installed within at least a portion of a reservoir, such as but not limited to a wall, cover, or bottom thereof. When so installed, the gas supply system is configured to generate a sanitizing gas (e.g., ozone) and to fluidly couple through the supply line to the reservoir of the hot beverage maker, such that sanitizing gas is conveyed to the reservoir and, in some instances, below any water in the reservoir. The exhaust system is configured to couple to the air in the reservoir, and to draw sanitizing gas (e.g. ozone) from the interior of the reservoir. In embodiments, the exhaust system includes a filter for converting or destroying the sanitizing gas removed from the interior of the reservoir.

Figure 1:
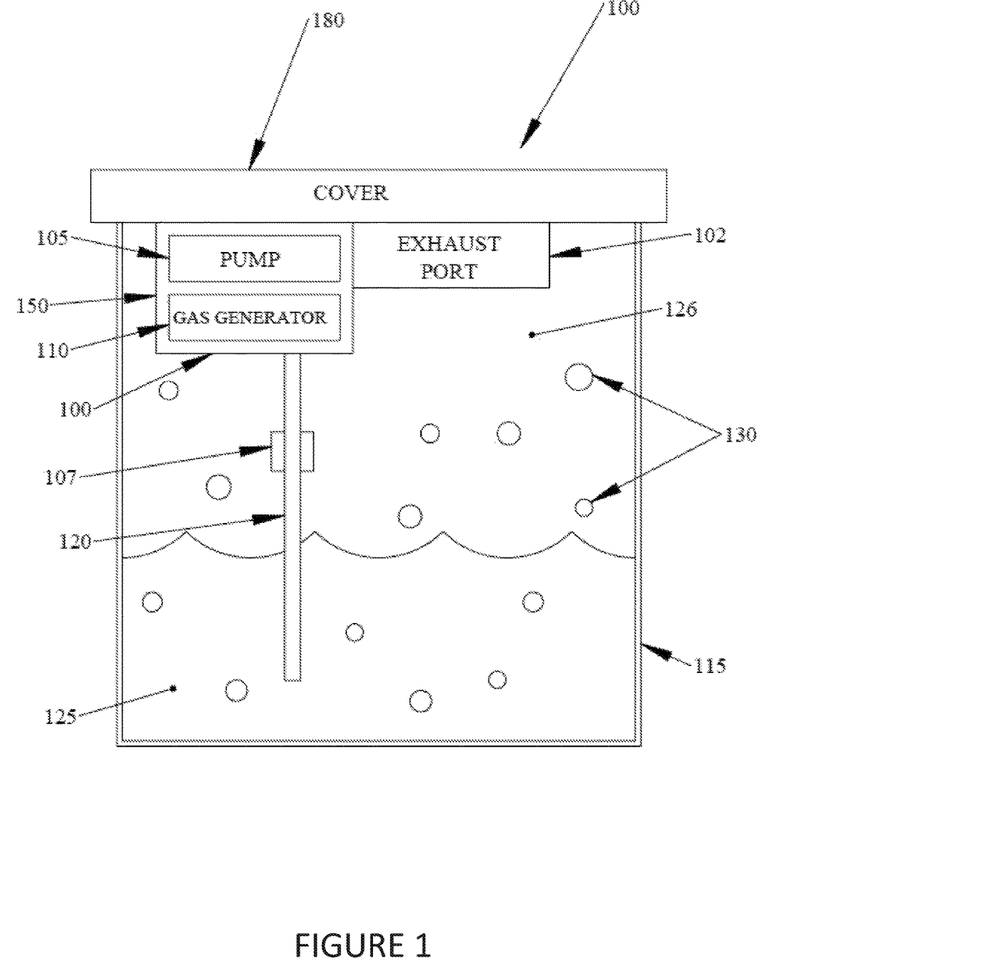
FIG. 1 is a block diagram of one example of a reservoir sanitization system, consistent with the present disclosure.

FIG. 1 is a block diagram of one example of a reservoir sanitization system consistent with the present disclosure. For the sake of illustration, FIG. 1 depicts an embodiment in which a reservoir sanitization system 100 is coupled to an interior wall of a cover 180 of a reservoir 115. It should be understood, however, that reservoir 115 is not required, and the reservoir sanitization systems described herein may be used with other containers and may be disposed at other locations. For example, reservoir sanitization system 100 may be coupled to a wall of reservoir 115 or another suitable container. In any case, coupling of the reservoir sanitization system to a reservoir may be accomplished using adhesive, ozone resistant sealant (e.g., silicone or acrylic), tape, mechanical fasteners, combinations thereof, and the like.

More specifically, FIG. 1 depicts an embodiment of a reservoir sanitization system that includes a water-proof or water resistant housing 150. A pump 105 and a gas generator (supply) 110 are disposed within the housing 150. The pump 105 (e.g., an air pump) is fluidly coupled to the gas generator 110, and is generally configured to generate a fluid flow (e.g., of air, sanitizing gas, or a combination thereof). The gas generator 110 is configured to generate a sanitizing gas 130, such as ozone. The gas generator 110 is fluidly coupled to a supply line 120. In operation, an air flow generated by pump 105 may convey the sanitizing gas 130 into the reservoir 115 via supply line 120.

In instances where liquid 125 (e.g., water) is present in the reservoir 115, the distal end of the supply line may be disposed positioned such that sanitizing gas 130 is introduced into the liquid. In such instances at least a portion of the sanitizing gas 130 may sanitize the liquid 125, as well as portions of the reservoir 115 that are below the level of the liquid 125. In addition, at least a portion of the sanitizing gas 130 may evolve from the liquid 125 into the air 126 within the reservoir 115 and sanitize the portion of the reservoir 115 that is above the level of the liquid 125.

Excess sanitizing gas 130 (if any) within the reservoir 115 may be converted to another composition and/or be removed from the interior of the reservoir 115 via an exhaust system 102. The exhaust system 102 may be connected to the reservoir sanitization system 100 via an adhesive, ozone resistant sealant such as silicone or acrylic, tape, mechanical fasteners, combinations thereof, or the like (not shown). In the embodiment of FIG. 1 the exhaust system 102 is shown as being separate from gas generator 110 and pump 105. It should be understood however that the exhaust system 102 may be integral with the other components of reservoir sanitization system 100, and/or may be disposed within housing 150. In any case, the exhaust system 102 may include an exhaust port and a filter. The filter may be configured to convert sanitizing gas to another composition, and/or to remove sanitizing gas in another manner. Activated carbon filters and magnesium oxide filters are examples of suitable filters that may be used in the exhaust system 102, and which can absorb sanitizing gas 103 and/or convert it to another composition.

The sanitizing gas system 100 may also include a desiccant (not separately shown). When used, the desiccant may function to remove moisture (e.g. water) from the air 126 within the reservoir 115, e.g., prior to its entry into pump 105. That may be useful when the air 126 is being used by gas generator 110 to generate a sanitizing gas such as ozone. In some embodiments, the desiccant is or includes activated carbon (e.g., an activated carbon filter), which may be the same or different from the filter used in exhaust system 102.

Sanitization system 150 may further include a sanitizing gas sensor (e.g., an ozone sensor), a display, and/or an alarm system. When used, such components may function to notify a user when a safe level of sanitizing gas 130 is present in the reservoir 115. In addition and as shown in FIG. 1, a check valve 107 may be present on or within the supply line 120, and may be configured to prevent the backflow of the liquid 125 (if any) into the supply line 120.

Although not shown in FIG. 1, the reservoir sanitization system may include or be coupled to a power supply. Any suitable power supply may be used, such as mains power, one or more batteries, solar power, combinations thereof, and the like.

Figure 2:
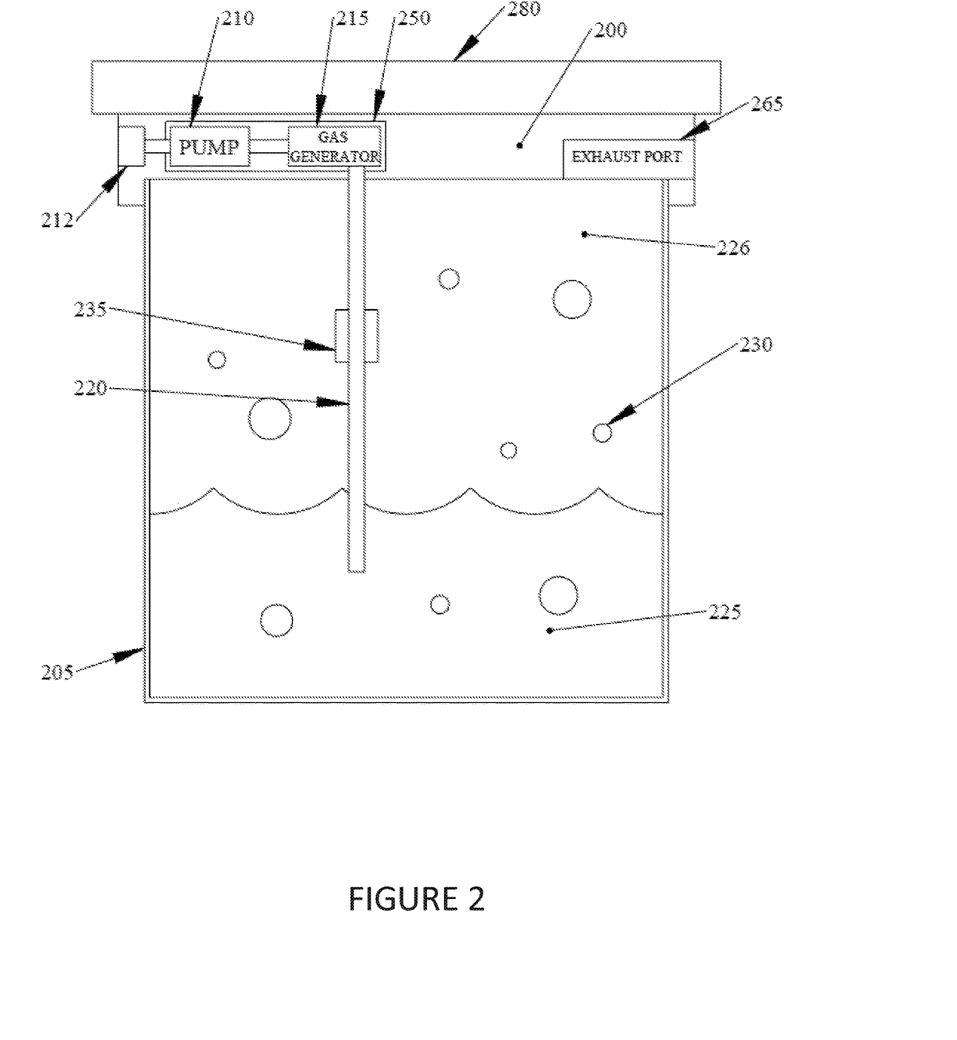
FIG. 2 is a block diagram of another example of a reservoir sanitization system consistent the present disclosure.

FIG. 2 is a block diagram of another example of a reservoir sanitization system 200 consistent with the present disclosure. As shown, the reservoir sanitization system 200 is configured to fit between a cover 280 of a reservoir 205 and a top rim formed by the walls of the reservoir 205. Like the embodiment of FIG. 1, the reservoir sanitization system 200 includes an air channel 212 that is fluidly coupled to a pump 210, which in turn is fluidly coupled to gas generator 215. The gas generator is configured to generate a sanitizing gas 230, such as ozone. The pump 210 (e.g., an air pump) is configured to drawn air into the air channel 212. The resulting air flow may be conveyed to the gas generator 215, and ultimately used to convey the sanitizing gas 230 to the interior of the reservoir 205.

More specifically and as shown in FIG. 2, a proximal end of a supply line 220 is fluidly coupled to the gas generator 215. The distal end of the supply line 220 is disposed within the reservoir 205. In instances where a liquid 225 is disposed in the reservoir, the distal end of the supply line 220 may be positioned below the surface of such liquid, e.g., as shown in FIG. 2. In any case, sanitizing gas 230 may be conveyed through supply line 220 into the reservoir 205. In some instances the sanitizing gas 230 may be released into the liquid 225. A portion of the sanitizing gas 230 may sanitizing the liquid 225, and a portion of the sanitizing gas may evolve from the liquid 225 to sanitize the air 226 and inner surfaces of the reservoir 205.

The sanitizing gas system 200 further includes an exhaust system 265. In these embodiments, all or a portion of the exhaust system may be removably coupled reservoir sanitization system 230 and or to cover 280. The exhaust system 265 may function to dispose of excess sanitizing gas that is present within the reservoir 205. In that regard, the exhaust system may include a pump that draws excess sanitizing gas 230 into a filter, wherein the filter is configured to absorb the sanitizing gas and/or to convert the sanitizing gas to another composition. In the case of ozone, for example, excess ozone within the reservoir 205 may be drawn into the exhaust system 265 and to a filter, which may absorb it and/or convert it to oxygen. In instances where the ozone is converted to oxygen, the oxygen may be exhausted into the environment via an exhaust port.

As further shown in FIG. 2 a check valve 235 may be coupled to supply line 220. When used, the check valve 220 may function to prevent backflow of liquid 225 into the supply line 220. And like the embodiment of FIG. 1, one or more sensors, displays, etc. (not shown) may be included in system 200. When used, the sensor(s) may function to sense the presence of sanitizing gas 230 within reservoir 205, and the display may function to alert a user when safe or unsafe levels of sanitizing gas 230 are present within the reservoir.

Figure 3:
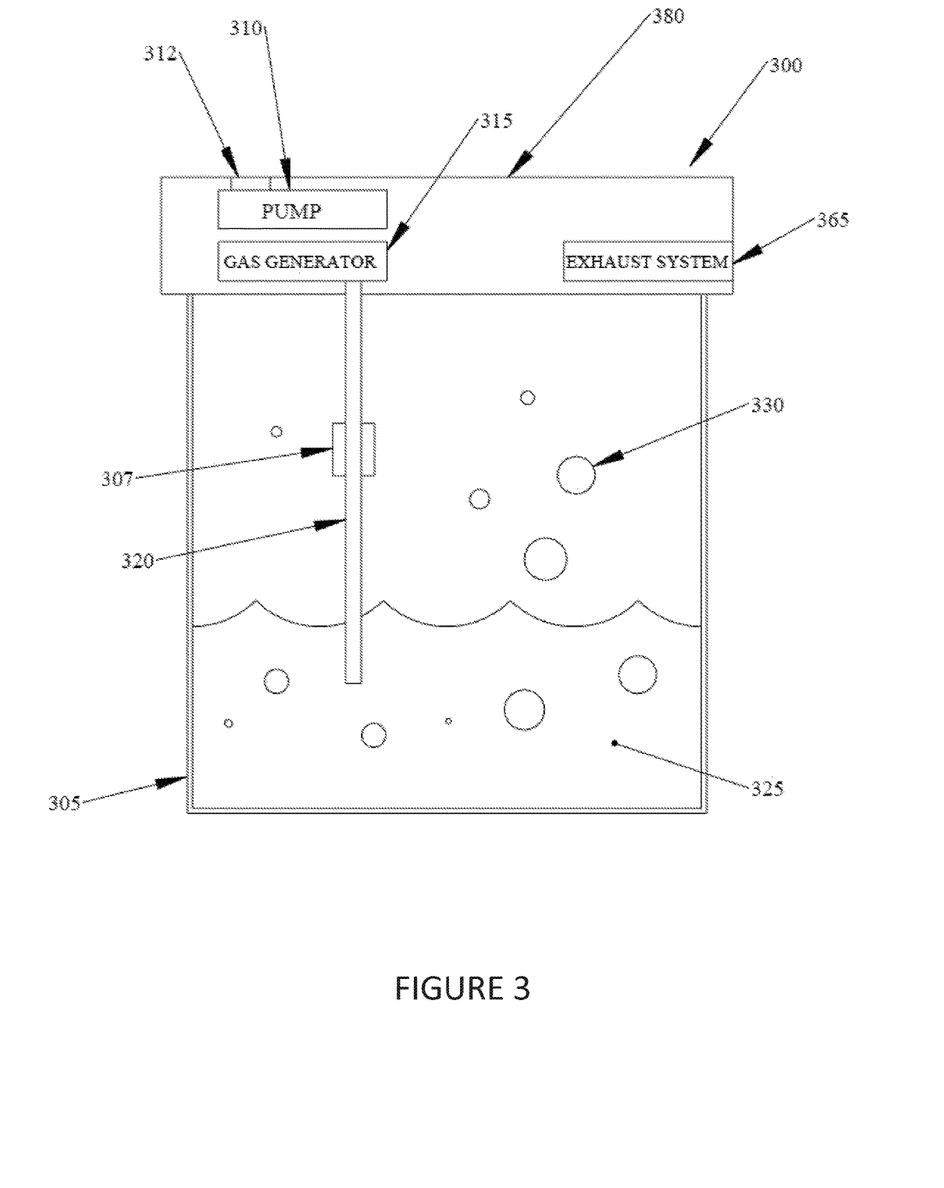
FIG. 3 is a block diagram of yet another example of a reservoir sanitization system consistent with the present disclosure.

FIG. 3 is a block diagram illustrating another example embodiment of a sanitizing gas system consistent with the present disclosure. In this embodiment the sanitizing gas system 300 is embedded in or otherwise integral with a cover 380 of a reservoir 305 of a hot beverage maker. As shown, a pump 310 is fluidly coupled to an air channel 312 formed in the top of the lid 380 at a proximal end. In addition, the pump 310 is fluidly coupled to a sanitizing gas generator 315. A proximal end of a supply line 320 is fluidly coupled to the gas generator 315. A distal end of the supply line 320 is disposed within the reservoir 305. When liquid 325 is present in the reservoir, the distal end may be disposed below the level of the liquid 325, as shown.

An exhaust system 365 may also be included in the sanitizing gas system 300. When included, the exhaust system may be removably coupled to the lid 380, and may function to absorb or convert excess sanitizing gas 330 to another composition, as described above on connection with FIGS. 1 and 2. Also like the embodiments of FIGS. 1 and 2, the sanitizing gas system may include a check valve 307, one or more sensors, and a display, the function of which is the same as previously described in connection with the other embodiments.

Another aspect of the present disclosure relates to methods for sanitizing a reservoir, such as but not limited to a reservoir of a hot beverage maker. In that regard reference is made to FIG. 4, which is a flow chart of example operations of one example of a reservoir sanitization method consistent with the present disclosure. As shown, the method 400 begins at block 401. The method may then advance to optional block 403, pursuant to which reservoir sanitization system with the present disclosure may be installed in the cover, placed between the cover and the body of the reservoir, or affixed to the bottom surface of the cover of a reservoir (e.g., of a hot beverage maker).

Figure 4:
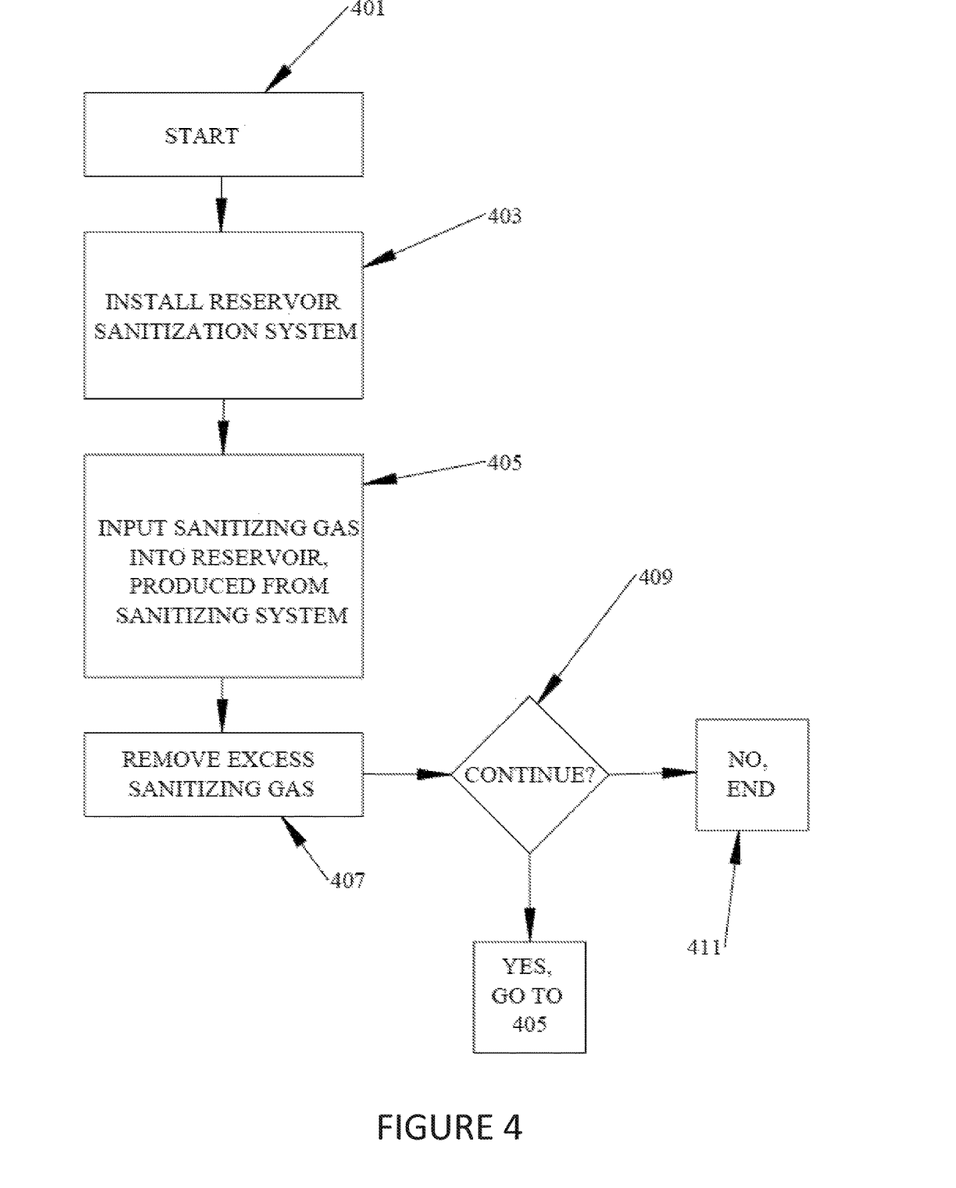
FIG. 4 is a flow chart of example operations of one example of a reservoir sanitization method consistent with the present disclosure.

Following the operations of block 403 or if block 403 is omitted (e.g. where a reservoir sanitization system is previously provisioned on, between or within a cover), the method may proceed to block 405. Pursuant to block 405 a sanitizing gas may be provided into a reservoir via a supply line e.g., as described above. Operations pursuant to block 405 may therefore include generating a sanitizing gas with a gas generator, and causing the sanitizing gas to flow into a supply line and into the reservoir, as previously described. At least a portion of the sanitizing gas so provided may sanitize the interior of the reservoir, including any liquid (e.g., water therein).

The method may then advance to block 407, pursuant to which excess sanitizing gas may be removed from the interior of the reservoir. Consistent with the foregoing description, operations pursuant to block 407 may include drawing sanitizing gas from the interior of the reservoir into an exhaust system. The operations pursuant to block 407 may also include conveying the sanitizing gas to a filter, as discussed above.

Following the operations of block 407 the method may proceed to block 409, pursuant to which a decision may be made as to whether the method is to continue. The outcome of the decision block 409 may be contingent on a sensor signal provided, e.g., by an optional sensor or on some other criteria. In any case if the method is to continue it may loop back to block 405, but if not, the method may proceed to block 411 and end.

The following examples pertain to additional non-limiting embodiments of the present disclosure.

EXAMPLE 1

According to this example there is provided a system for sanitizing a hot beverage maker with a water reservoir including: a reservoir sanitization system configured to supply a sanitizing gas, wherein the reservoir sanitization system is further configured to couple to a bottom surface of a cover for the water reservoir; an air pump fluidly coupled to a sanitization gas generator; a supply line coupled to the gas generator, wherein the supply line is fluidly coupled to the gas generator at a proximal end, with a distal end immersed below any water in the water reservoir; and an exhaust system configured to remove the sanitizing gas.

EXAMPLE 2

This example includes any or all of the features of example 1, and further includes a desiccant, wherein the desiccant is configured to remove moisture from the air in the reservoir prior to its entry into air pump.

EXAMPLE 3

This example includes any or all of the features of example 1 wherein the exhaust system further comprises a removable activated carbon filter.

EXAMPLE 4

This example includes any or all of the features of example 1 and further includes a check valve coupled to the supply line.

EXAMPLE 5

This example includes any or all of the features of example 1, and further includes a silicone adhesive on a surface of the reservoir sanitization system, wherein the adhesive is configured to affix the reservoir sanitization system to the bottom surface of a cover of the water reservoir and also affixes to the reservoir sanitization system.

EXAMPLE 6

This example includes any or all of the features of example 1, and further includes a sensor for sensing the sanitizing gas.

EXAMPLE 7

This example includes any or all of the features of example 1, and further includes a display.

EXAMPLE 8

According to this example there is provided a system for sanitizing a hot beverage maker with a reservoir including: a reservoir sanitization system configured to supply a sanitizing gas, wherein the reservoir sanitization system configured to be disposed between a cover of the reservoir and a top rim of walls of the reservoir; wherein the sanitization system comprises: an air pump fluidly coupled to an air channel at a proximal end and to a sanitization gas generator at a distal end; a supply line coupled to the gas generator, wherein the supply line is fluidly coupled to the gas generator at a proximal end, with a distal end immersed below any water in the water reservoir; and an exhaust system configured to remove the sanitizing gas.

EXAMPLE 9

This example includes any or all of the features of example 8, wherein the exhaust system comprises a removable activated carbon filter.

EXAMPLE 10

This example includes any or all of the features of example 8, wherein the exhaust system comprises a removable magnesium oxide filter.

EXAMPLE 11

This example includes any or all of the features of example 8, and further includes a check valve couple to the supply line.

EXAMPLE 12

This example includes any or all of the features of example 8, and further includes a sensor for sensing sanitization gas in the reservoir.

EXAMPLE 13

This example includes any or all of the features of example 8, and further includes a display for notifying a user with safe-use instructions.

EXAMPLE 14

According to this example there if provided a system for sanitizing a hot beverage maker with a reservoir including a lid configured to cover an opening defined by wall of the reservoir, wherein: the lid comprises a reservoir sanitization system; the reservoir sanitization system comprises an air pump coupled to a sanitization gas generator, an exhaust system, and a supply line; a proximal end of the supply line is fluidly coupled to the gas generator; a distal end of the supply line is disposed within the reservoir; and the exhaust system is configured to remove sanitizing gas introduced into the reservoir by the gas generator via the supply line.

EXAMPLE 15

This example includes any or all of the features of example 14, wherein the exhaust system comprises a removable activated carbon filter.

EXAMPLE 16

This example includes any or all of the features of example 14, wherein the exhaust system comprises a removable magnesium oxide filter.

EXAMPLE 17

This example includes any or all of the features of example 14, and further includes a check valve coupled to the supply line.

EXAMPLE 18

This example includes any or all of the features of example 14, and further includes a sensor for sensing the sanitizing gas.

EXAMPLE 19

This example includes any or all of the features of example 14, and further includes a display.

EXAMPLE 20

According to this example there is provided a method for sanitizing a hot beverage maker with a reservoir, including: installing a reservoir sanitization system within a reservoir, between a reservoir and a lid of the reservoir, or within the lid of the reservoir, the reservoir sanitization system including an air pump, a gas generator, a supply line, and an exhaust system; generating a sanitizing gas with the gas generator; conveying the sanitizing gas into the reservoir via the supply line; and exhausting sanitizing gas from the reservoir via the exhaust system.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A system for sanitizing a hot beverage maker with a water reservoir comprising:
    a reservoir sanitization system configured to couple to a bottom surface of a cover for the water reservoir the reservoir sanitization system comprising;
        an air pump fluidly coupled to a sanitization gas generator;
        a supply line comprising a proximal end coupled to the gas generator and a distal end disposed within an interior of the water reservoir; and
        an exhaust system configured to remove the sanitizing gas;
    wherein in operation, the sanitization gas generator generates a sanitizing gas that flows into the interior of the water reservoir via the supply line.

2. The system of claim 1, further comprising a desiccant, wherein the desiccant is configured to remove moisture from the air in the reservoir prior to its entry into air pump.

3. The system of claim 1 wherein the exhaust system further comprises a removable activated carbon filter.

4. The system of claim 1 further including a check valve coupled to the supply line.

5. The system of claim 1, further including a silicone adhesive on a surface of the reservoir sanitization system, wherein the adhesive is configured to affix the reservoir sanitization system to the bottom surface of a cover of the water reservoir and also affixes to the reservoir sanitization system.

6. The system of claim 1 further comprising a sensor for sensing said sanitizing gas.

7. The system of claim 1 further comprising a display.

8. A system for sanitizing a hot beverage maker with a reservoir comprising:
    a reservoir sanitization system configured to be disposed between a cover of the reservoir and a top rim of walls of the reservoir; wherein the reservoir sanitization system comprises:
        an air pump fluidly coupled to an air channel at a proximal end and to a sanitization gas generator at a distal end;
        a supply line comprising a proximal end coupled to the sanitization gas generator and a distal end disposed within an interior of the water reservoir; and
        an exhaust system configured to remove the sanitizing gas;
    wherein in operation, the sanitization gas generator generates a sanitizing gas that flows into the interior of said water reservoir via said supply line.

9. The system of claim 8, wherein the exhaust system comprises a removable activated carbon filter.

10. The system of claim 8, wherein the exhaust system comprises a removable magnesium oxide filter.

11. The system of claim 8, further comprising a check valve couple to the supply line.

12. The system in accordance with claim 8 further comprising a sensor for sensing sanitization gas in the reservoir.

13. The system in accordance with claim 8 further comprising a display for notifying a user with safe-use instructions.

14. A system for sanitizing a hot beverage maker with a reservoir comprising a lid configured to cover an opening defined by wall of the reservoir, wherein:
    the lid comprises a reservoir sanitization system;
    the reservoir sanitization system comprises an air pump coupled to a sanitization gas generator, an exhaust system, and a supply line;
    a proximal end of the supply line is fluidly coupled to the sanitization gas generator;
    a distal end of the supply line is disposed within an interior of the reservoir;
    the exhaust system is configured to remove sanitizing gas; and
    in operation, the sanitization gas generator generates a sanitizing gas that flows into the interior of the water reservoir via the supply line.

15. The system of claim 14, wherein the exhaust system comprises a removable activated carbon filter.

16. The system of claim 14, wherein the exhaust system comprises a removable magnesium oxide filter.

17. The system of claim 14, further comprising a check valve coupled to the supply line.

18. The system of claim 14, further comprising a sensor for sensing the sanitizing gas.

19. The system of claim 14, further comprising a display.

20. A method for sanitizing a hot beverage maker with a reservoir, comprising:
    installing a reservoir sanitization system within a reservoir, between a reservoir and a lid of the reservoir, or within the lid of the reservoir, the reservoir sanitization system comprising an air pump, a sanitization gas generator, a supply line, and an exhaust system;
    generating a sanitizing gas with the sanitization gas generator;
    conveying the sanitizing gas into an interior of the reservoir via the supply line; and
    exhausting sanitizing gas from the reservoir via the exhaust system.

* * * * *

UNITED STATES PATENT AND TRADEMARK OFFICE
CERTIFICATE OF CORRECTION

PATENT NO. : 10,524,613 B2
APPLICATION NO. : 15/499167
DATED : January 7, 2020
INVENTOR(S) : Timothy Leyva et al.

Page 1 of 1

It is certified that error appears in the above-identified patent and that said Letters Patent is hereby corrected as shown below:

On the Title Page

In Column 1, under (71) Applicant, delete "MA", and insert -- NH --, therefor.

In Column 2, under (57) Abstract, Line 5, delete "a the" and insert -- the --, therefor.

Signed and Sealed this
Third Day of March, 2020

Andrei Iancu
*Director of the United States Patent and Trademark Office*